United States Patent
Liska et al.

(10) Patent No.: US 6,632,315 B2
(45) Date of Patent: Oct. 14, 2003

(54) METHOD OF MANUFACTURING A MICRODIALYSIS CATHETER

(76) Inventors: Jan Liska, Sibyllegatan 53, S-114 43 Stockholm (SE); Anders Franco-Cereceda, Rörstrandsgatan 4, S-113 40 Stockholm (SE)

( * ) Notice: Subject to any disclaimer, the term of this patent is extended or adjusted under 35 U.S.C. 154(b) by 276 days.

(21) Appl. No.: 09/826,956

(22) Filed: Apr. 6, 2001

(65) Prior Publication Data

US 2001/0015253 A1 Aug. 23, 2001

Related U.S. Application Data

(62) Division of application No. 09/076,808, filed on May 13, 1998.

(30) Foreign Application Priority Data

Mar. 11, 1998 (SE) ................................. 9800791

(51) Int. Cl.[7] ............................................. B29C 47/00
(52) U.S. Cl. ........................... 156/244.13; 156/244.18; 156/257; 264/145; 264/154
(58) Field of Search ........................ 156/244.13, 244.18, 156/257; 264/145, 154, 209.1, 209.3

(56) References Cited

U.S. PATENT DOCUMENTS

| | | | |
|---|---|---|---|
| 4,694,832 A | | 9/1987 | Ungerstedt |
| 5,106,365 A | * | 4/1992 | Hernandez ............... 604/27 |
| 5,191,900 A | * | 3/1993 | Mishra ................... 600/585 |
| 5,353,792 A | * | 10/1994 | Lubbers et al. ........... 600/311 |
| 5,441,481 A | * | 8/1995 | Mishra et al. ............ 604/29 |
| 5,607,390 A | * | 3/1997 | Patsalos et al. ........... 604/29 |
| 5,718,678 A | * | 2/1998 | Fleming, III ............. 604/43 |
| 5,735,832 A | * | 4/1998 | Karlsson ................. 604/524 |
| 5,810,789 A | * | 9/1998 | Powers et al. ............ 604/523 |
| 6,264,627 B1 | * | 7/2001 | Liska et al. .............. 604/29 |

OTHER PUBLICATIONS

Huxtable "Federation Proceedings vol. 39, No. 9 Jul. 1980", pp. 2685–2690.
Thorac. Cardiovasc. Surgeon 41 (1993) pp. 93–100.
European Heart Journal (1987) 8, 206–207.
Journal of Neuroscience Methods 60 (1995) 151–155.
Microdialysis of Human Tissue in Vivo pp. E218–E220.
D.G. Maggs et al. Brain and Skeletal Muscle Microdialysis pp. S75–S82.
Acra Physiol Scand 1997, 159, 261–262.
Swedish Article, Stockholm I Apr. 1995.
Journal of Cerebral Blood Flow and Metabolism vol. 5, No. 3, 1985.

* cited by examiner

*Primary Examiner*—Mark Eashoo
(74) *Attorney, Agent, or Firm*—Birch, Stewart, Kolasch & Birch, LLP

(57) ABSTRACT

A method of manufacturing a microdialysis catheter, comprises the steps of extruding a flexible material to form an elongate catheter body having a substantially cylindrical outer surface and a plurality of continuous internal channels extending in the longitudinal direction of said catheter body; sealing a free end of said catheter body; providing in said surface at a distance from said free end an opening extending into said catheter body to communicate with a portion of a first of said channels; providing communication between said first channel and a second of said channels at a distance from said free end shorter that said distance; and covering said opening by a microdialysis membrane.

4 Claims, 2 Drawing Sheets

METHOD OF MANUFACTURING A MICRODIALYSIS CATHETER

This application is a divisional of application Ser. No. 09/076,808, filed on May 13, 1998, the entire contents of which are hereby incorporated by reference and for which priority is claimed under 35 U.S.C. §120; and this application claims priority of Application No. 9800791-7 filed in Sweden on Mar. 11, 1998 under 35 U.S.C. §119.

FIELD OF THE INVENTION

The invention relates to a method of manufacturing a microdialysis catheter to be inserted into and guided by a blood vessel of a living being.

BACKGROUND OF THE INVENTION

Microdialysis is used to monitor the interstitial fluid in various body organs with respect to local metabolic changes. To perform Microdialysis, a catheter is used including an elongate flexible body having at least two internal channels therealong, and, at its distal end, a dialysis chamber. U.S. Pat. No. 4,694,832 to Ungerstedt discloses a dialysis probe provided in a distal end of an elongate, flexible hose. The probe consists of several elements that have to be carefully assembled and mounted at a free end of the hose during manufacture of the microdialysis catheter. This involves a substantial risk that the various elements come loose when the catheter is in use. Furthermore, the brittle microdialysis membrane is not internally supported well enough to make this known microdialysis probe suitable for insertion into and guidance by a blood vessel, mounted in the end of the flexible hose.

SUMMARY OF THE INVENTION

It is an object of the invention to set aside these drawbacks by proposing a method of manufacturing a microdialysis catheter that is robust, simple to insert in a vessel, and has a simple construction.

According to the present invention there is provided a method of manufacturing a microdialysis catheter, comprising the steps of extruding a flexible material to form an elongate catheter body having a substantially cylindrical outer surface and a plurality of continuous internal channels extending in the longitudinal direction of said catheter body; sealing a free end of said catheter body; providing in said surface at a distance from said free end an opening extending into said catheter body to communicate with a portion of a first of said channels; providing communication between said first channel and a second of said channels at a distance from said free end shorter that said distance; and covering said opening by a microdialysis membrane.

BRIEF DESCRIPTION OF THE DRAWINGS

Two embodiments of the present invention will be described hereinafter, reference being made to the accompanying drawings, wherein.

DESCRIPTION OF THE PREFERRED EMBODIMENTS

Figure 1:
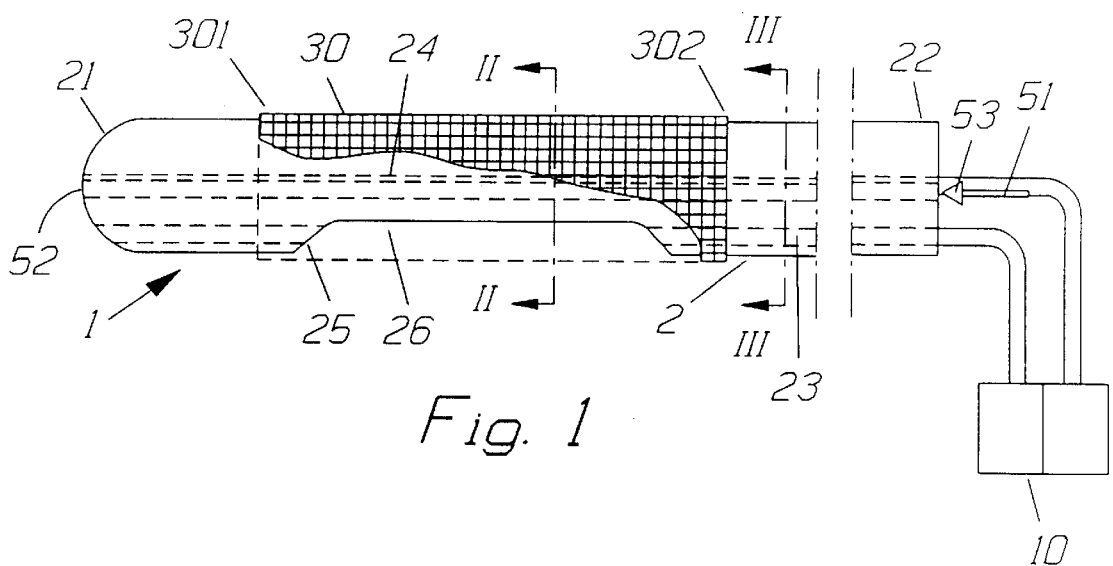
FIG. 1 is a partly broken diagrammatic view of a first embodiment of a catheter according to the invention.

It is to be noted that like or corresponding parts are designated by like reference numerals throughout the drawings.

FIG. 1 is a partly broken diagrammatic view of a first embodiment of a catheter 1 according to the invention. The catheter comprises an elongate catheter body 2 having an essentially cylindrical outer surface, a distal end 21, and a proximal end 22, between which it preferably is continuous, except for the openings, which will be explained below. The catheter body 2 is preferably made of radio opaque PVC or other suitable material, and its outer diameter is preferably in the range of 5–7,5 Fr ($\approx$1,5–2,5 mm).

Figure 3:
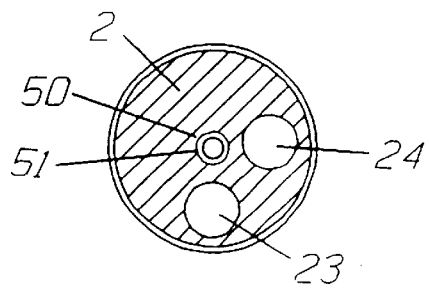
FIG. 3 is a cross sectional view taken at III—III in FIG. 1.

As seen in FIG. 3, which is a cross section taken at III—III in FIG. 1, the catheter body 2 includes a number of longitudinal channels. Two of the channels 23, 24 are designed for circulating dialysis solution, and at their proximal ends they are connectable to means 10 for circulating, monitoring or analyzing, and preferably collecting the dialysis solution. In the figure, the channels 23, 24 are shown to have the same inner diameters. However, the channels can have different inner diameters, and their cross sections can have different shapes than the shown. In the case of different inner diameters, channel 24 preferably has the smaller, and dialysis solution flows from the means 10 through channel 24 and back through channel 23.

Figure 2:
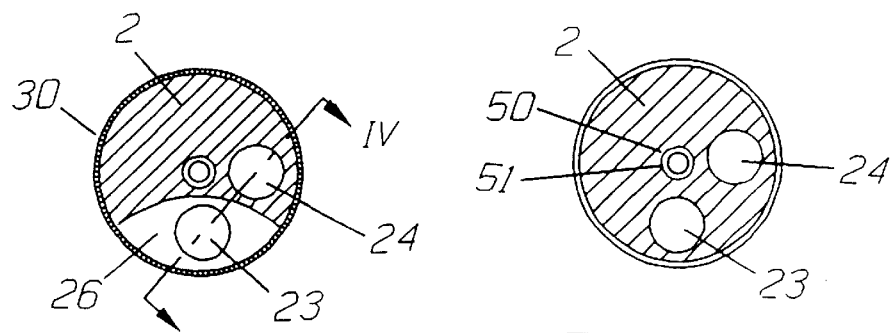
FIG. 2 is a cross sectional view taken at II—II in FIG. 1.

At a distance from its distal end, the catheter body has an opening 25, which is best seen in FIGS. 1 and 2. The form of the opening 25 in the outer surface of the catheter body 2 can for example be circular, oval or essentially rectangular. The length of the opening 25, in the longitudinal direction is preferably 10–30 mm. The opening in the catheter body 2 can be formed by removing a part of its wall by cutting away a portion of the catheter body 2 in a wall region of channel 23, whereby a section of channel 23 is opened, and thus a space or chamber 26 is formed. As will be explained further below, the chamber 26 is provided with a wall formed by a microdialysis membrane 30, in order to provide a microdialysis chamber 26. Preferably the chamber 26 is enlarged in this section by the removal of the wall part, as shown in the figures. A part of or the whole circumference of said region can be cut away to further enlarge the chamber 26 and thus enlarge the dialysis surface.

Figure 4:
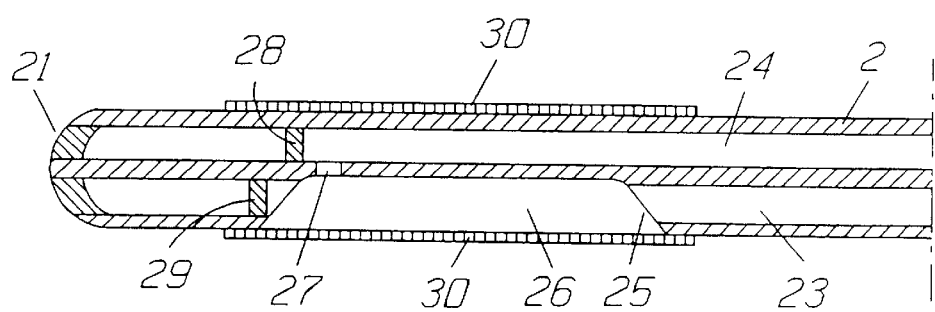
FIG. 4 is a longitudinal section taken at IV—IV in FIG. 2.

In FIG. 4, which is a longitudinal section taken at IV—IV in FIG. 2, it is shown that channels 23 and 24 are connected by a channel or opening 27 between the chamber 26 and channel 24, so that dialysis solution can flow between the channels. The channel or opening 27 is preferably arranged so as to connect a distal portion of the chamber 26 and the channel 24, but other placements could also be possible. Preferably the channels 23 and 24 are plugged or sealed between channel 27 and the distal end of the catheter body 2, by means of a plug or a seal 28, 29, in order to prevent dialysis solution from entering channels 23, 24 beyond channel 27. Further, channels 23 and 24 are plugged or sealed at the distal end 21 of the catheter body 2.

In a region around the opening 25 the catheter body 2 is provided with microdialysis membrane 30 having a socket-like shape, and surrounding a portion of the catheter body 2. In FIG. 1 the microdialysis membrane 30 is partly broken up, so that the opening 25 and the chamber 26 can be seen. The microdialysis membrane 30 can be slid on to the catheter body 2 over the distal end 21. At regions of its edges 301, 302 the microdialysis membrane 30 is further bonded or fastened with a glue or adhesive, or by other suitable means to the catheter body 2, in order to prevent any liquid to enter or exit between the microdialysis membrane 30 and the catheter body 2 from or to the outside.

Possibly, the catheter body 2 can be provided with an annular recess, for receiving the microdialysis membrane 30, in said region surrounding the opening 25.

Depending on the substances to be detected at the microdialysis, a microdialysis membrane 30 of cuprophane, polycarbonate or PES (molecular cut-off between 1–200 kD) can be used. In order to prevent triggering of coagulation when in contact with blood, the microdialysis membrane 30 may be surface heparinized.

To facilitate the insertion of the catheter 1 into a certain blood vessel, a guide wire channel 50, for receiving a guide wire 51, can be arranged in the catheter body 2. The distal end of the catheter body 2 is closed or sealed except for an opening 52. This opening 52 forms a continuation of the inner surface of the guide wire channel 50. The guide wire 51 is used during insertion of the catheter, to increase the stiffness of the catheter 1, and to make it possible to bend the catheter 1 into a desired curve, in order to facilitate its insertion. After insertion of the catheter 1 the guide wire 51 is removed, and a blood sample can be taken out at the proximal end of the catheter 1 through the opening 52 and the guide wire channel 50. To prevent the guide wire 51 from passing through the opening 52 the guide wire 51 is provided with a stop 53.

The catheter body 2 can advantageously be manufactured from an extruded continuous profile body. The profile body is cut to a desired length, and the channels, except the guide wire channel, are sealed or plugged at their distal ends. Further the microdialysis chamber is formed by cutting, the channel between the channels (microdialysis chamber and channel) is formed, and the blind ends of the channels are sealed or plugged. Thereafter the catheter body 2 is provided with a microdialysis membrane, and connections or connection tubes at the proximal end.

The distal portion of the catheter may be preformed into a desired curvature so that by torquing the catheter about its longitudinal axis, the catheter can be manipulated to the desired location.

The preform is also advantageous in that, it helps the catheter to remain in the right position when once correctly located.

Figure 5:
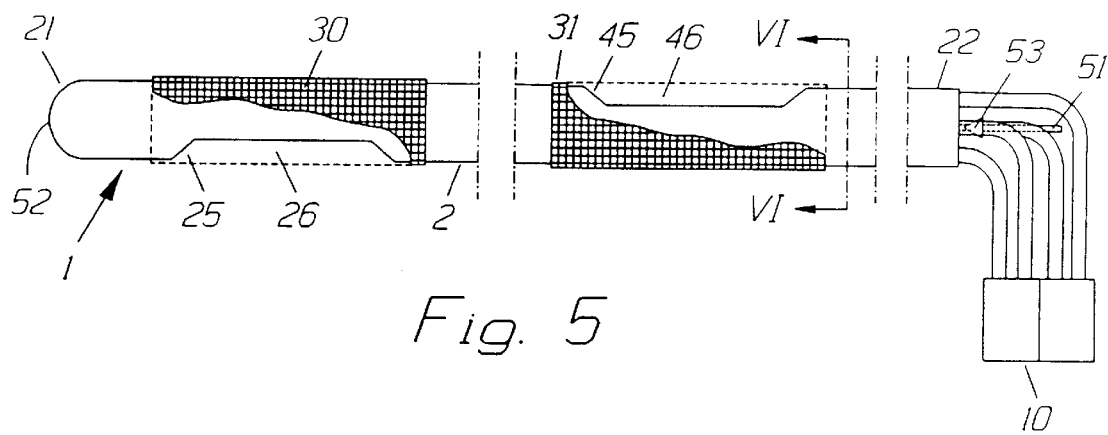
FIG. 5 is a partly broken diagrammatic view of a second embodiment of a catheter according to the invention.
Figure 7:
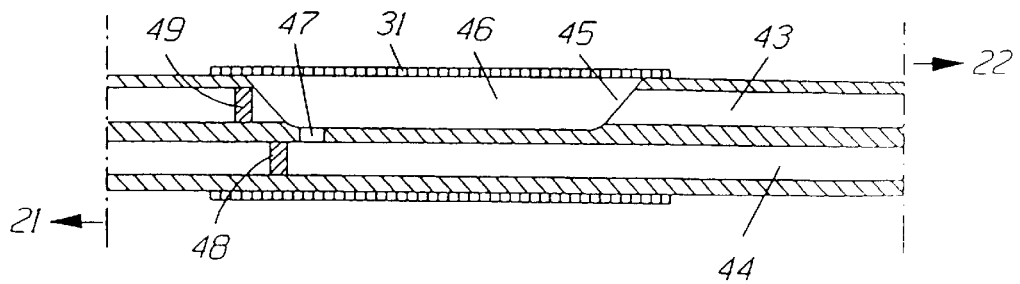
FIG. 7 is a longitudinal section taken at VII—VII in FIG. 5.

In FIG. 5 a second embodiment of a catheter according to the invention is shown. This catheter includes a first microdialysis chamber 26, with associated channels 23, 24, a first opening 25 and a first microdialysis membrane 30, as described in connection to the first embodiment according to FIG. 1. At a center distance of about 100–120 mm from the first opening 25 in the catheter body 2, in the direction towards the proximal end 22, a second opening 45 is provided in the catheter body 2, located on the opposite side to the first opening 25. As seen in FIGS. 5 and 7, a second microdialysis chamber 46 with associated second microdialysis membrane 31, and channels 43, 44, is arranged in connection with the second opening 45, in the same manner as in the first embodiment. Channels 43, 44 are connected by means of a channel 47, preferably at the distal portion of the second microdialysis chamber, and the channels 43, 44 are preferably sealed or plugged 48, 49 to prevent dialysis solution to enter the portions of the channels between channel 47 and the distal end of the catheter body 2, in the same manner as in the first embodiment. The two channels 43, 44 are connected at their proximal ends to the same means 10, for circulating, monitoring or analyzing, and preferably collecting the dialysis solution, as the two channels 23, 24, or to separate means.

Figure 6:
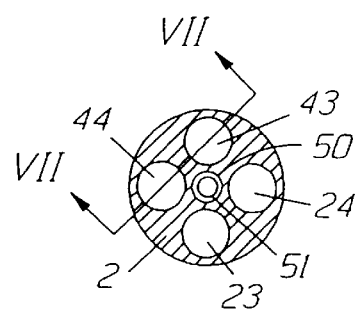
FIG. 6 is a cross sectional view taken at VI—VI in FIG. 5.

FIG. 6 is a cross sectional view taken at VI—VI in FIG. 5, showing a possible placement of the two channels 23, 24, the two channels 43, 44, the guide wire 51, and the guide wire channel 50 inside the catheter body 2.

Although the invention has been described in conjunction with two preferred embodiments, it is to be understood that various modifications may still be made without departing from the spirit and scope of the invention, as defined by the appended claims. For example the dimensions can vary, depending on the specific use.

What is claimed is:

1. A method of manufacturing a microdialysis catheter, comprising the steps of:

a) extruding a flexible material to form an elongate catheter body having a substantially cylindrical outer surface and a plurality of continuous internal channels extending in the longitudinal direction of said catheter body;

b) sealing a free end of said catheter body;

c) providing in said surface at a distance from said free end an opening extending into said catheter body to communicate with a portion of a first of said channels;

d) providing communication between said first channel and a second of said channels at a distance from said free end shorter that said distance; and e) covering said opening by a microdialysis membrane.

2. The method according to claim 1, wherein said opening is formed by cutting.

3. The method according to claim 1, wherein said opening is formed by cutting away a wall portion of said catheter body in a wall region of one of said channels, thereby opening a section of said channel to provide a microdialysis chamber.

4. The method according to claim 3, wherein said channel is enlarged by removal of a wall part.

* * * * *